United States Patent
Dattagupta et al.

(12) 
(10) Patent No.: US 6,379,930 B1
(45) Date of Patent: Apr. 30, 2002

(54) STABILIZATION OF NUCLEIC ACID AMPLIFICATION COCKTAILS

(75) Inventors: Nanibhushan Dattagupta; C. Nagaraja Sridhar; Whei-Kuo Wu, all of San Diego, CA (US)

(73) Assignee: Applied Gene Technologies, Inc., San Diego, CA (US)

( * ) Notice: Subject to any disclaimer, the term of this patent is extended or adjusted under 35 U.S.C. 154(b) by 0 days.

(21) Appl. No.: 09/384,717

(22) Filed: Aug. 26, 1999

Related U.S. Application Data

(60) Provisional application No. 60/146,579, filed on Jul. 30, 1999.

(51) Int. Cl.[7] .......................... C12P 19/34; C12Q 1/68; C07H 19/00; C07H 21/04; C07H 21/02
(52) U.S. Cl. .................... 435/91.2; 435/6; 435/91.1; 536/22.1; 536/23.1; 536/24.3; 536/24.31; 536/24.32; 536/24.33
(58) Field of Search .................. 435/6, 91.1, 91.2; 536/22.1, 23.1, 24.3, 24.31, 24.32, 24.33

(56) References Cited

U.S. PATENT DOCUMENTS

| | | |
|---|---|---|
| 4,582,798 A | 4/1986 | Sheldon, III et al. |
| 4,683,195 A | 7/1987 | Mullis et al. |
| 4,683,202 A | 7/1987 | Mullis et al. |
| 4,737,454 A | 4/1988 | Dattagupta et al. |
| 5,026,840 A | 6/1991 | Dattagupta et al. |

(List continued on next page.)

OTHER PUBLICATIONS

Chaires, et al., "Parsing the Free Energy of Anthracycline Antibiotic Binding to DNA," *Biochem.*, 35:2047–2053 (1996).

Chaires, et al., "Structures–Based Design of a New Bisintercalating Anthracycline Antibiotic," *J. Med. Chem.*, 40:261–266 (1977).

Cimino, et al., "Post–PCR sterilization: a method to control carryover contamination for the polymerase chain reaction", *Nucleic Acid Res.*, 19(1):99–107 (1990).

Dattagupta, et al., "Nucleic Acid Hybridization: a rapid method for the diagnosis of infectious diseases," (G.G. Jackson, H.D. Schlumberger and H.J. Zeiler, Eds.) Friedr. Vieweg & Sohn Verlagsgesellschaft mbH, Braunschweig, 241–247 (1989).

Della–Latta, et al., "Comprehensive Evaluation of Performance, Laboratory Application, and Clinical Usefulness of Two–Direct Amplification Technologies for the Detection of *Mycobacterium tuberculosis* Complex", *Am. J. Clin. Pathol.*, 110:301–310 (1998).

Gelmini, et al., "Quantitative polymerase chain reaction–based homogeneous assay with fluorogenic probes to measure c–erbB–2 oncogene amplification," *Clin. Chem.*, 43(5):752–758 (1997).

Haq, et al., "Specific Binding of Hoechst 33258 to the d(CGCAAATTTGCG)$_2$ Duplex: Calorimetric and Spectroscopic Studies", *J. Mol. Biol.*, 271:244–257 (1997).

Heim, et al., "Highly sensitive detection of gene expression of an intronless gene: amplification of mRNA, but not genomic DNA by nucleic acid sequence based amplification (NASBA)", *Nucleic Acids Res.*, 26(9):2250–2251 (1998).

Hu, et al., "Analytic Performance and Contamination Control Methods of a Ligase Chain Reaction DNA Amplification Assay for Detection of *Chlamydia trachomatis* in Urogenital Specimens", *Diagn. Microbiol. Infect. Dis.*, 24:71–76 (1996).

Marmur, "A Procedure for the Isolation of Deoxyribonucleic Acid from Micro–organisms", *J. Mol. Biol.*, 3:208–218 (1961).

Moore, et al., "Detection and Identification of *Mycobacterium tuberculosis* Directly from Sputum Sediments by Ligase Chain Reaction", *J. Clin. Microbiol.*, 36(4):1028–1031 (1998).

Nazarenko, et al., "A closed tube format for amplification and detection of DNA based on energy transfer", *Nucleic Acids Res.*, 25(12):2516–2521 (1997).

Neumaier, et al., "Fundamentals of quality assessment of molecular amplification methods in clinical diagnostics", *Clin. Chem.*, 44(1):12–26 (1998).

Oehlenschlager, et al., "Detection of HIV–1 RNA by nucleic acid sequence–based amplification combined with fluorescence correlation spectroscopy", *Proc. Natl. Acad. Sci. (USA)*, 93:12811–12816 (1996).

Pao, et al., "Inhibition of in vitro enzymatic DNA amplification reaction by ultra–violet light irradiation", *Molec. and Cell. Probes*, 7:217–219 (1993)

Rys, et al., "Preventing False Positives: Quantitative Evaluation of Three Protocols for Inactivation of Polymerase Chain Reaction Amplification Products", *J. Clin. Microbiol.*, 31(9):2356–2360 (1993).

Tevere, et al., "Detection of *Mycobacterium tuberculosis* by PCR Amplification with Pan–*Mycobacterium* Primers and Hybridization to an M. *tuberculosis*–Specific Probe", *J. Clin. Microbiol.*, 34(4):918–923 (1996).

Troesch, et al., "*Mycobacterium* Species Identification and Rifampin Resistance Testing with High–Density DNA Probe Arrays", *J. Clin. Microbiol.*, 37(1):49–55 (1999).

(List continued on next page.)

*Primary Examiner*—Jeffrey Siew
(74) *Attorney, Agent, or Firm*—Morrison & Foerster LLP

(57) ABSTRACT

The present invention provides a cocktail of reagents for nucleic acid amplification that are stabilized by inclusion of a reversible inhibitor of undesirable reactions. Such cocktail of reagents eliminates the requirement for separate preparation and quality control of each reagent used in a reaction. Methods to prepare stabilized cocktails and to use stabilized cocktails also are included. The stabilized cocktail compositions also can include reagents to release nucleic acid from cells and to label the nucleic acid, allowing detection of nucleic acid in a sample with a single reagent addition step. The invention also provides kits for performing the above methods.

23 Claims, No Drawings

U.S. PATENT DOCUMENTS

| | | | |
|---|---|---|---|
| 5,221,608 A | | 6/1993 | Cimino et al. |
| 5,348,855 A | | 9/1994 | Dattagupta et al. |
| 5,409,818 A | | 4/1995 | Davey et al. |
| 5,532,145 A | * | 7/1996 | Tessman et al. ............ 435/91.2 |
| 5,554,517 A | | 9/1996 | Davey eta l. |
| 5,565,339 A | * | 10/1996 | Bloch et al. ................ 435/91.2 |
| 5,614,387 A | * | 3/1997 | Shen et al. ................. 435/91.2 |
| 5,792,614 A | | 8/1998 | Western et al. |
| 6,110,490 A | * | 8/2000 | Thierry ......................... 424/50 |
| 6,153,412 A | * | 11/2000 | Park et al. .................. 435/91.2 |
| 6,187,566 B1 | * | 2/2001 | Dattagupta et al. ........ 435/91.1 |

OTHER PUBLICATIONS

Vaneechoutte, et al., "The possibilities and limitations of nucleic acid amplification technology in diagnostic microbiology", *J. Med. Microbiol*, 46:188–194 (1997).

Walder, et al., "Use of PCR primers containing a 3'–terminal ribose residue to prevent cross–contamination of amplified sequences", *Nucleic Acids Res.*, 21(18):4339–4343 (1993).

Walker, et al., "Strand displacement amplification—an isothermal, in vitro DNA amplification technique," *Nucleic Acids Res.*, 20(7):1691–1696 (1992).

Whelen, et al., "Direct Genotypic Detection of *Mycobacterium tuberculosis* Rifampin Resistance in Clinical Specimens by Using Single–Tube Heminested PCR", *J. Clin. Microbiol.*, 33(3):556–561 (1995).

Wylie, et al., "Comparative Evaluation of Chlamydiazyme, PACE 2, and AMP–CT Assays for Detection of *Chlamydia trachomatis* Endocervical Specimens", *J. Clin. Microbiol.*, 36(12):3488–3491 (1998).

* cited by examiner

STABILIZATION OF NUCLEIC ACID AMPLIFICATION COCKTAILS

This application claims priority benefit of U.S. Provisional Patent Application Serial No. 60/146,579, filed Jul. 30, 1999, under 35 U.S.C. §119(e). The disclosure of the above-described application is incorporated herein by reference in its entirety.

FIELD OF THE INVENTION

This invention relates to the field of nucleic acid detection and, more specifically, to the preparation of stabilized cocktails of reagents for nucleic acid amplification.

BACKGROUND OF THE INVENTION

Nucleic acid detection through modern molecular biological techniques has revolutionized diagnosis of infections, cancer, inborn genetic errors, HLA typing, and forensic and paternity testing. Diagnosis is accomplished through any of a variety of nucleic acid detecting methods, including, for example, the polymerase chain reaction (PCR), ligase chain reaction (LCR), transcription mediated amplification (TMA) reaction, nucleic acid sequence based amplification (NASBA) reaction, and strand displacement amplification (SDA) reaction.

Reagents used in nucleic acid detection methods are typically prepared separately as individual stock solutions and are combined to produce the cocktail just prior to its use. For example, in PCR, a cocktail of reagents contains a DNA polymerase, appropriate nucleoside triphosphates, primer(s), and an amplification buffer. Typically, the cocktail of reagents cannot be stored at 4° C. for an extended period of time, but must be made fresh just before use to avoid undesirable reactions during storage between the individual reagents such as non-specific DNA polymerization of the nucleoside triphosphates in the absence of a target template.

The requirement to prepare and quality control separate stock solutions of each reagent used in amplification increases the costs of nucleic acid detection in the clinical lab. Also, the requirement to add several reagents to make the cocktail just before use increases the likelihood of error in the clinical lab. Thus, there is a need for a stabilized cocktail of nucleic acid detection reagents that is stable for extended times at 4° C.

SUMMARY OF THE INVENTION

Accordingly, it is an object of the present invention to eliminate the requirement for separate preparation and quality control of each reagent used in a nucleic acid amplification reaction by providing a cocktail of the reagents in which undesirable reactions during storage between the reagents are avoided.

To accomplish this and other objectives, there has been provided, according to one aspect of the present invention, a composition comprising a cocktail of reagents for performing nucleic acid amplification that avoids undesirable reactions during storage between the individual reagents, thereby stabilizing the cocktail upon storage, comprising one or more of the reagents necessary to perform nucleic acid amplification and an inhibitory concentration of a reversible inhibitor(s) of the undesirable reaction.

According to one embodiment, the cocktail of reagents comprises one or more of a nucleic acid polymerase or ligase and one or more of a nucleoside triphosphate(s), nucleic acid primer(s) and an amplification buffer.

According to another embodiment, the cocktail of reagents comprises a lipid, which can be in the form liposomal vesicles wherein the cocktail of reagents is encapsulated within the liposomes.

According to yet another embodiment, the cocktail of reagents comprises all the reagents necessary to perform a nucleic acid amplification reaction.

According to another embodiment, the inhibitor of the undesirable reactions upon storage is a nucleic acid binding ligand. The binding ligand can be an intercalator compound, which can be monoadduct forming. The intercalator compound can be a furocoumarin such as 4'-aminomethyltrioxsalen ("AMT") or angelicin, or a phenanthridine. The binding ligand also can be a non-intercalating compound such as benzimides, netropsins and distamycins.

According to another embodiment of the present invention, a method of nucleic acid amplification is provided using the composition comprising a stabilized cocktail of reagents.

According to yet another embodiment of the present invention, a method for preparing a stabilized cocktail of reagents which avoids undesirable reactions that occur between the reagents upon storage is provided. The method includes adding the inhibitor(s) of the undesirable reactions to the cocktail of reagents, wherein the inhibitor is added to the cocktail at a concentration that is inhibitory to the reaction but at a concentration which will be non-inhibitory when the cocktail is later diluted for its intended use. The method further includes adding a lipid for releasing nucleic acid from cells. In such cases, the lipid is used to produce liposomal vesicles and the stabilized cocktail of reagents and the inhibitor are encapsulated within the vesicles.

According to still yet another embodiment, the method for preparing a stabilized cocktail of reagents includes reagents suitable for performing polymerase chain reaction, ligase chain reaction, transcription based amplification reaction, nucleic acid sequence based amplification reaction and strand displacement amplification reaction.

According to another embodiment of the invention, the method of preparing a stabilized cocktail is for a transcription based or amplification reaction or a ligase chain reaction and said inhibitor(s) is phosphate ion.

According to yet another embodiment, the method for preparing a stabilized cocktail includes a binding ligand as the inhibitor. The binding ligand can be an intercalator compound, which can be monoadduct forming. The intercalator compound can be a furocoumarin such as AMT. The binding ligand also can be a non-intercalating compound.

According to still yet another aspect of the present invention, kits for performing nucleic acid amplification using the stabilized cocktail of reagents are provided.

DETAILED DESCRIPTION OF THE INVENTION

The present invention provides novel compositions and methods for preparing a cocktail of reagents that avoids undesirable reactions during storage between the reagents by addition of a reversible inhibitor of the reaction. Such undesirable reactions include, for example, formation of primer dimers, degradation of primers by exonuclease activity of the polymerase and non-specific polymerization of nucleoside triphosphates and/or primers.

The reagent cocktail is stable because of the presence of the inhibitor, thus allowing the cocktail to be stored for later use in amplification. Amplification is achieved when the cocktail is appropriately diluted with the target template such that the concentration of reaction inhibitor is below its effective level while the concentration of the other reagents are at an effective level. The use of stabilized cocktail of reagents eliminates the cost of preparation and quality control associated with preparing individual stock solutions of each reagent required for a particular nucleic acid extraction and/or detection.

General Definitions

Oligonucleotide: Low molecular weight deoxyribo-, ribo-, copolymers of deoxyribo- and ribonucleic acids of chain lengths between 3 and 150. Such oligonucleotides can have modified nucleotide residues such as —O-methoxy, phosphorothio-, methylphosphonates and others known in art.

Primers: Usually oligonucleotides which are used for extension reaction by a nucleic acid polymerase after a template primer hybrid is formed. Such primers can carry sequences specific for transcription by an RNA polymerase.

Nucleic Acid Probe: Nucleic acid with substantially complementary sequences to the target nucleic acids for detection or capture from a mixture. Such probes can be labeled for detection or immobilized onto a solid support to enrich the target by capture. A probe can be an single stranded or partially double stranded and can be an oligonucleotide or a larger nucleic acid.

Membrane fluidizing compound: A chemical substance that renders a cell membrane fluid or flexible to facilitate release of cellular material into solution or uptake of extracellular contents. Compounds that induce pinocytosis in addition to fluidizing the membrane also are included within the meaning of a membrane fluidizing compound as used herein. A membrane fluidizing compound can be a lipid or a non-lipid and can be ionic or non-ionic. Membrane fluidizing compounds generally do not cause cell death at lower concentrations that effect membrane fluidity, however, cell death typically results at higher concentrations of the compound.

Lipid: Any of various substances that are soluble in non-polar organic solvents (such as chloroform and ether), that with proteins and carbohydrates constitute the principal structural components of living cells, and that include fats, waxes, phosphatides, cerebrosides, and related and derived compounds.

Liposome vesicles: A vesicle composed of one or more concentric phospholipid bilayers. The structure of the liposomes may be as a multilamellar vesicle (MLV), a small unilamellar vesicle (SUV), a large unilamellar vesicle (LUV). A liposome is formed from a single lipid or combination of lipids (i.e., lipsosmal formulation) and optionally other compounds.

Thiocationic lipid: A lipid molecule with sulfur substitution and which is positively charged at neutral pH.

Photoreagent or photoactive reagents: Reagents which under appropriate wavelengths of light exposure form a covalent bond with nucleic acid.

Preferred Embodiments

The present invention provides compositions comprising a cocktail of reagents for performing nucleic acid amplification that avoids undesirable reactions during storage between the individual reagents, thereby stabilizing the cocktail upon storage. Such composition comprises one or more of the reagents necessary to perform nucleic acid amplification and an inhibitory concentration of a reversible inhibitor(s) of the undesirable reaction. The inhibitor is added to the cocktail at a concentration that is inhibitory to the reaction, but at a concentration that will be non-inhibitory when the cocktail is later diluted for its intended use. The cocktail of reagents generally includes a nucleic acid polymerase, a reversible inhibitor(s) of the undesirable reaction and one or more of a nucleoside triphosphate(s), nucleic acid primer(s) and an amplification buffer.

Inhibitors of amplification reactions which are suitable for use in stabilizing a cocktail of amplification reagents include, for example, reagents well known in the art as amplification inhibitors. For example, phosphate ion is inhibitory for a transcription mediated amplification reaction (Della-Latta, et al., *J. Clin. Microbiol.*, 37:1234–1235 (1999)). An inhibitory concentration of phosphate ion for a transcription mediated reaction is about 0.7 mM. In addition, phosphate ion above 1.2 mM is inhibitory for a ligase chain reaction (Notomi, et al., *J. Clin. Pathol.*, 51:306–308, (1998)). Certain polysaccharides, heme and components present in urine also inhibit amplification reactions (Mahony, et al., *J. Clin. Microbiol.*, 36:3122–26 (1998); Moreira, *Nucleic Acids Res.*, 26(13):3309–10 (1998)). These reversible inhibitors can be added to cocktails in the present invention to stabilize the components upon storage prior to use of the cocktail in amplification as described above.

Stabilized amplification cocktails of the invention are stable upon storage at 4° C. for 24 hours (hrs), more preferably for 48 hrs, still more preferably for 72 hrs and most preferably for more than one week. Stabilized amplification cocktails of the invention also are stable upon storage at 25° C. preferably for 8 hrs and more preferably for 24 hrs.

The present invention provides a composition comprising a cocktail for amplification containing 250 mM of phosphate ion. In this mixture no amplification will occur and all the reagents will remain inactive and stable. Amplification can later be achieved by diluting the composition ten fold during preparation of an amplification reaction mixture. At 25 mM phosphate, the amplification reaction will not be inhibited.

The present invention also provides compositions for stabilizing a cocktail where the reversible inhibitor has nucleic acid binding properties such as intercalators like furocoumarins, phenanthridines, acridines, phenazines or non-intercators like netropsin, distamycin and others. Representative intercalating agents suitable as inhibitors include azidoacridine, ethidium monoazide, ethidium diazide, ethidium dimer azide (Mitchell, et al., *J. Am. Chem. Soc.*, 104:4265 (1982)), and 4-azido-7-chloroquinoline, and 2-azidofluorene. A specific nucleic acid binding azido compound has been described by Forster, et al., *Nucleic Acid Res.*, 13:745 (1985). Such compounds include nucleic acid binding ligands as described herein for labeling nucleic acid (i.e., light activated compounds: "LACs"). The present invention provides a method for reversibly inhibiting a PCR amplification using the inhibitor, 4'-aminomethyltrioxsalen ("AMT"), which is a nucleic acid binding ligand.

Inhibitors that are DNA binding ligands also can include additional substituents that are useful for other aspects of nucleic acid detection, provided that the substituents do not impair the inhibitory nature of the compound. For example, photoreactive forms of intercalating agents such as the azidointercalators are useful as both an inhibitor of the undesirable reaction in reagent preparation and for labeling a nucleic acid covalently upon photoactivation. Other useful inhibitors that are photoreactable intercalators include the furocoumarins which form (2+2) cycloadducts with pyrimidine residues, alkylating agents such as bis-chloroethylamines and epoxides or aziridines, e.g., aflatoxins, polycyclic hydrocarbon epoxides, mitomycin and norphillin A.

Specific LACs which can be used as reversible inhibitors to stabilize amplification cocktails include, 4'-Biotinyl-PEG-4,5'-dimethylangelicin (BPA: Example 17)), Angelicin-DAPI-Biotin (BDA: Example 21)), bisbenzimidazole-PEG-azidonitrobenzene (AZPIMA: Example 20)), Angelicin-bisbenzimidazole-PEG-acridine ("APIMA"), Angelicin-bisbenzimidazole-PEG-biotin (BPIMA: Example 19) and compounds described in U.S. Pat. Nos. 4,950,744 and 5,026,840. In such compounds, PEG represents any molecular weight or polymer substituent that is known to comprise polyethyleneglycol, including pentaoxaheptadecane.

The desired concentration of each inhibitor in the composition for stabilization can be determined by one skilled in the art using known methods. For example, it is helpful to first determine the concentration of inhibitor at which inhibition of undesirable reactions during storage occur and the concentration at which the inhibitor does not affect labeling. Once the dilution range between inhibition and non-inhibition is established, this dilution then dictates the fold concentration necessary of the cocktail of labeling reagents. The concentration of the labeling reagent in the mixture is preferably about 10 fold higher than the concentration at which the inhibitor allows an amplification reaction to yield a detectable amplification product, although concentrations of 20 fold to 50 fold also are useful.

In some embodiments, the cocktail of reagents also includes a lipid to form a liposomal vesicle or other structure to encapsulate the cocktail. In this approach, the microenvironment of the liposomal vesicle or other structure allows the inhibitor to be at a sufficiently high concentration to stabilize the reagents. When the cocktail including the lipid is used for amplification, it is diluted such that the vesicles or other structure is disrupted, thus releasing the reagents and reducing the inhibitor concentration below that which causes inhibition.

Prior methods of forming liposomes and encapsulating aqueous solution are applicable for preparing the nucleic acid releasing compositions of the present invention (e.g., Olson, et al., *Biophys. Acta,* 557:9 (1979)). For example, prior art liposomal formulations used to encapsulate hemoglobin (e.g., U.S. Pat. No. 4,911,929) are to produce liposomal vesicles as described herein. Such liposomal formulation contains roughly equivalent quantities of cholesterol and phosphatidylcholine, with 5 to 10% negatively charged lipid, such as phosphatidic acid, dicetyl phosphate, or dimyristoyl phosphatidyl glycerol (DMPG). Hydration of the dried lipid film results in formation of multi-lamellar vesicles (MLV), which can be extruded at low-pressure (e.g., 50–90 psi) through filters of progressively smaller pore size to large unilamellar vesicles (LUVs). Once the liposomal vesicles are formed, any unencapsulated aqueous solution can be removed, if desired, by centrifugation or diafiltration and then recycled.

Lipid used for the formation of the liposome can be natural or synthetic and include phospholipids, glycolipids, and lipid related compounds. Exemplary lipids include, lecithin (phosphatidylcholine), phosphatidylethanolamine, phosphatidic acid, phosphatidylserine, phosphatidylinositol, phosphatidylglycerol, sphingomyelin, cardiolipin, and hydrogenated derivatives thereof, which can be used either alone or in combinations. The glycolipids include cerebroside, sulfolipid (e.g., sulfatide), and ganglioside. The structure of the liposomes may be as a multilamellar vesicle (MLV), a small unilamellar vesicle (SUV), or large unilamellar vesicle (LUV).

To stabilize the lipid, an antioxidant such as tocopherol (vitamin E) can be added to the solution. A suitable amount of an antioxidant is about 0.01 to 0.5% by weight based on the weight of the phospholipid. The liposome composition of the invention also can contain, as a stabilizer, a high molecular weight polymer such as albumin, dextran, vinyl polymers, non-ionic surface active agents, gelatin, and hydroxyethyl starch.

Lipid used for the formation of the liposome can be natural or synthetic and include phospholipids, glycolipids, and lipid related compounds. Exemplary lipids include, lecithin (phosphatidylcholine), phosphatidylethanolamine, phosphatidic acid, phosphatidylserine, phosphatidylinositol, phosphatidylglycerol, sphingomyelin, cardiolipin, and hydrogenated derivatives thereof, which can be used either alone or in combination. The glycolipids include cerebroside, sulfolipid (e.g., sulfatide), and ganglioside. The structure of the liposomes may be as a multilamellar vesicle (MLV), a small unilamellar vesicle (SUV), or large unilamellar vesicle (LUV).

To stabilize the lipid, an antioxidant such as tocopherol (vitamin E) can be added to the solution. A suitable amount of an antioxidant is about 0.01 to 0.5% by weight based on the weight of the phospholipid. The liposome composition of the invention also can contain as a stabilizer, a high molecular weight polymer such as albumin, dextran, vinyl polymers, non-ionic surface active agents, gelatin, and hydroxyethyl starch.

Liposomal vesicles that encapsulate stabilized cocktails as used herein can be prepared by a variety of known methods. For example, conventionally used hydration, reversed phase evaporation, removal of surfactant, solvent injection, freeze-thawing and dehydration-rehydration can be employed.

In the hydration method, the selected lipids are dissolved in an organic solvent (e.g., chloroform and ether), which is non-denaturing, and the solvent is evaporated from the resulting solution yield a thin homogeneous film. An aqueous solution containing the stabilized cocktail is added to the thin membrane, and the mixture is subjected to agitation and sonication to yield a liposome preparation encapsulating the aqueous solution. The aqueous solution contains a buffer at a pH between 4 and 11. The pH of the buffer is chosen such that when the lipids or liposomes are added to an assay medium, the final pH in a range suitable to preserve nucleic acids in solution.

In the reversed-phase evaporation method, the selected lipids are dissolved in an organic solvent (e.g., chloroform and ether), as discussed above, and are added to the aqueous solution containing the stabilized cocktail and subjected to agitation, sonication and high pressure homogenization to uniformly disperse the aqueous solution. The solvent is evaporated from this dispersion to yield a liposome preparation encapsulating the aqueous solution.

In the removal of surfactant approach, the selected lipids dissolved in organic solvent are mixed with a surfactant (e.g., cationic surfactant such as cholic acid or deoxycholic acid, and a non-ionic surfactant such as Triton X-100 and octyl-D-glucoside) and added to the aqueous solution containing the stabilized cocktail, which is followed by agitation, sonication and high pressure homogenization to uniformly disperse the aqueous solution. The surfactant is then removed by dialysis, gel filtration and ultrafiltration, which are applied singly or in combination.

In the solvent injection, approach, the selected lipids are dissolved in organic solvent and are added to the aqueous solution containing the stabilized cocktail, which has been set for a temperature about 10° C. higher than the boiling point of the organic solvent. Then, the organic solvent is evaporated.

A composition of the invention comprising a stabilized nucleic acid amplification cocktail also can comprise reagents useful for releasing nucleic acid from a cell sample in a form suitable for directly detecting the nucleic acid as described in U.S. Provisional Patent Application entitled "Sample Processing to Release Nucleic Acids for Direct Detection" by Dattagupta et al., filed Jul. 30, 1999. The a reagent cocktail can include primers, enzymes, nucleoside triphosphates, deoxynucleoside triphosphates and other components as needed for amplification and appropriate reagents to release the nucleic acid. In this approach, a single addition of the stabilized cocktail with the lipid reagents can be added to a cell sample and release and amplification of a target nucleic acid can be achieved without further reagent addition. This can be accomplished because the added lipids are non-denaturing and non-inhibitory of nucleic acids or proteins used in nucleic acid release, amplification, labeling or detection.

Reagents useful for releasing nucleic acid without denaturation include an aqueous solution that comprises a water and/or other water miscible solvent and further includes a buffer to stabilize the pH between 4 and 11, with the ultimate pH depending on the stability of the nucleic acid to be released.

The aqueous solution comprising one or more lipids or a liposomal formulation includes those lipids suitable for releasing cellular or otherwise inaccessible nucleic acid without denaturation. Liposomal formulations containing cationic lipids that have been used for delivery of oligonucleotides and other agents to target cells are useful for releasing nucleic acid from cells without denaturation as provided herein. PCT WO 96/40627 and U.S. Pat. Nos. 5,851,548, 5,759,519, 5,756,352, and 5,739,271 teach liposomal formulations containing cationic lipids.

The lipid containing vesicles or other structures used in the present compositions for releasing nucleic acid from cells include complex mixtures of different lipophilic substituents. Such complex mixtures allow for optimization of the physical properties of the liposomes, such as pH sensitivity, temperature sensitivity and size. For example, in certain embodiments, dioleoylphosphatidylethanolamine ("DOPE"), and other pH sensitive amphiphilic compounds can be used to formulate liposomes which destabilize at acidic pH. This promotes fusion of the liposome with endosomal membranes when exposed to the degradative acidic pH and enzymatic contents of the endosome, resulting in release of the contents of the endosome into the cytoplasm. (Ropert, et al., *Biochem. Biophys. Res. Comm.* 183 (2):879–895 (1992); Juliano, et al., *Antisense Res. and Dev.* 2:165–176 (1992)). Although not wishing to be bound by any particular theory, it is believed that pH controlled degradation of liposomes in the cytoplasm of the cell enhances release of nucleic acids.

Lipids for releasing nucleic acid from cells also can include sterols to enhance stability of liposomal vesicles both in vitro and in vivo. In particular, organic acid derivatives of sterols, such as cholesterol or vitamin $D_3$, which have been reported to be easier to formulate than their non-derivatized water-insoluble equivalents (e.g., U.S. Pat. Nos. 4,721,612 and 4,891,208), are useful in preparing liposomal formulations as described herein.

Preferred lipids for use in the present compositions and methods are cationic lipids (i.e., derivatives of glycerolipids with a positively charged ammonium or sulfonium ion-containing headgroup), including those useful in liposomal formulations for the intracellular delivery of negatively charged biomolecules such as oligonucleotides. The useful-ness of cationic lipids may be derived from the ability of their positively charged headgroups to interact with negatively charged cell surfaces, although this is not known for certain. The cationic lipid N-(1-(2,3-dioleyloxy)propyl)-N,N,N-trimethylammonium chloride ("DOTMA") as described by Felgner, et al., *Proc. Natl. Acad. Sci. (USA)* 84:7413–7417 (1987) (see also U.S. Pat. No. 4,897,355) is a cationic lipid with an ammonium group that can be used in lipid formulations in the compositions of the invention. In such formulations, DOTMA may bind to DNA through an ionic lipid-DNA complex that assists in releasing nucleic acid from a cell.

Other ammonium ion-containing cationic lipid formulations that can be used in the nucleic acid releasing compositions of the present invention include the DOTMA analog, 1,2-bis(oleoyloxy)-3(trimethylammonio)propane ("DOTAP") (Stamatatos, et al., *Biochemistry*, 27:3917–3925 (1988)); the 5lipophilic derivative of spermine (Behr, et al., *Proc. Natl. Acad. Sci. (USA)*, 86:6982–6986 (1989)); and cetyltrimethylammonium bromide (Pinnaduwage, et al., *Biochem. Biophys. Acta*, 985:33–37 (1989); see Leventis, et al., *Biochem. Biophys. Acta*, 1023:124–132 (1990); Zhou, et al., *Biochem. Biophys. Acta*, 1065:8–14 (1991); Farhood, et al., *Biochem. Biophys. Acta*, 1111:239–246 (1992); and Gao, et al., *Biochem. Biophys. Res. Comm.*, 179:280–285 (1991)). Cationic lipids are commercially available including DOTMA (Gibco BRL, Bethesda, Md.), DOTAP (Boehringer Mannheim, Germany), and 1,2-diacyl-3-trimethylammonium propane ("TAP") (Avanti Polar Lipids, Alabaster, Ala.).

Cationic lipids containing sulfonium ions (i.e., thiocationic lipids) also can be used in combination with a stabilized cocktail to release nucleic acid. Sulfonium ions have entirely different physical properties than ammonium ions, which provides sulfonium cationic lipids with some unique properties. Ammonium ion-containing compounds are classified as hard bases, because the nitrogen atom possesses high electronegativity, is difficult to polarize and oxidize, and the valence electrons are held tightly by the nucleus. This characteristic may account for some of the toxicity associated with ammonium ion-containing lipid formulations. In contrast, sulfonium ion-containing compounds are classified as soft bases, because the sulfur atom possesses low electronegativity, is easy to polarize and oxidize, and the valence electrons are held more loosely by the nucleus. This decreased charge density exhibited by sulfonium ion-containing (i.e. "thiocationic") lipids may effectuate an enhanced interaction with negatively charged cellular membranes, as well as a decreased toxicity, leading to compositions with increased ability to release cell nucleic acid in a non-denatured form.

Cationic lipids with relatively small polar headgroups as described by Felgner, et al., *J. Biol. Chem.*, 269(4): 2550–2561 (1994), can be particularly useful in the present compositions for releasing nucleic acids. However, the sulfonium ion type cationic lipid, which has a relatively larger headgroup, also can be useful because of the physiochemical properties associated with the sulfonium ion. A lipid headgroup that consists of a sulfur atom surrounded by adjoining saturated carbon atoms exhibits a diffusion of charge to the neighboring carbon atoms that can facilitate interaction of the lipid with cellular membranes, as well as decrease the toxicity of the lipid (U.S. Pat. No. 5,759,519).

The liposome preparations used in combination with the stabilized cocktail of reagents for amplification also can include a positively charged surface by including in the formulation, saturated or unsaturated aliphatic amines including, e.g., stearylamine and oleylamine, sphingosine, phosphatidylethanolamine, N-(1-(2,3-dioleyloxy)propyl)-N, N,N-trimethylammoniumchloride, cholesterylhemisuccinate, 3β-(N-(N',N'-dimethylaminoethane)carbamoyl)cholesterol and cholesteryl(4'-trimethylammonio)butanoate, with preference given to stearylamine and sphingosine as described in U.S. Pat. No. 5,759,519.

The stabilized cocktail including reagents for releasing nucleic acid also can include, for example, substances other than lipids that enhance release of nucleic acid depending on the nature of the sample and the environment in which the nucleic acid is contained (e.g., the type of cell). Such nucleic acid releasing substances include, for example, an enzyme (s) to degrade cell structure, a non-ionic membrane fluidizing compound(s), and/or a metal chelator(s).

Enzymes suitable for use with lipid containing aqueous solution are available from natural sources or produced by recombinant DNA methods. Such enzymes include, for example, lysozyme, lipases, and proteinases such as proteinase K, pronase, trypsin and chymotrypsin. Lysozymes from bovine, chicken, human and lipases from wheat germ, human, yeast and other sources also are suitable enzymes to degrade cell structure. These enzymes preferably are nuclease free to support stability of released nucleic acids in solution. The aqueous solution containing lipids and enzymes for releasing nucleic acid can be encapsulated into a liposome, if desired.

The enzymes are used at a molar ratio of lipid to enzyme of between 10,000: 1 and 1:10,000. The optimal ratio of enzyme to lipid can be readily determined by one skilled in the art. This can be accomplished by mixing target cells with various lipid:enzyme ratios, and determining the effectiveness of releasing nucleic acid in a probe hybridization assay.

Non-ionic membrane fluidizing compounds, which have been described in Suciu et al., *Mol. Microbiol.*, 21:181–95 (1996), Nabekura, et al., *Pharm. Res.*, 13(7):1069–72 (1996), and Lindow, et al., *Cryobiol.*, 32(3):247–258 (1995), and include aromatic alcohols such as all phenyl, napthyl, and higher alcohols, also can be used to release nucleic acid from cells without denaturation of enzymes or proteins. The hydrocarbon side chains of aromatic alcohols can be from $C_1$ to $C_{50}$ and longer, preferably between $C_1$ and $C_{20}$. The —OH residue can be at the $C_n$ terminus carbon for a primary alcohol or any place as in a secondary or tertiary alcohol. The C—C bonds in $C_n$ chain in addition to single bond can have unsaturated linkages in the form of double or triple bonds. The carbon chain also can have secondary and tertiary C-linkages. Phenethyl alcohol, sec-phenethyl alcohol, benzyl alcohol are examples of non-ionic membrane fluidizing compounds.

Non-ionic membrane fluidizing compounds can be included in the stabilized cocktail of reagents so as to enhance release of nucleic acids from cells without creating an enzyme or protein inhibitory environment. Such compounds can be present in the aqueous solution at a concentration between 0.001% and 10.0% . The final concentration of non-ionic membrane fluidizing compound in a sample for releasing nucleic acid is preferably between about 0.001 and 10% (v/v), more preferably between 0.01% and 5%, most preferably between 0.1% and 2%. The ultimate concentration of the non-ionic membrane fluidizing compound depends on the nature of the fluidizing compound and the other components of the nucleic acid releasing composition. One skilled in the art can readily determine the proper concentration of membrane fluidizing compound for effective release of nucleic acid from a particular sample by determining binding of a specific probe to nucleic acid released by a particular formulation.

The aqueous solution of the nucleic acid releasing composition also can include metal chelators such as ethylenediaminetetraacetic acid (EDTA) and ethyleneguaninetetraacetic acid (EGTA). In addition, the aqueous solution can be heated to enhance release of the nucleic acid essentially as described in U.S. Pat. No. 5,837,452.

The present invention also provides methods for preparing a stabilized cocktail of reagents which avoids undesirable reactions during storage and for using such compositions for amplifying a nucleic acid. The stabilized cocktail of reagents, as discussed above, is useful for amplification in virtually any amplification format, including, for example, the polymerase chain reaction, ligase chain reaction, transcription based amplification reaction, nucleic acid sequence based amplification reaction and strand displacement amplification reaction.

Amplification methods suitable for use with the present methods include, for example, polymerase chain reaction (PCR), ligase chain reaction (LCR), transcription mediated amplification (TMA) reaction, nucleic acid sequence based amplification (NASBA) reaction, and strand displacement amplification (SDA) reaction. These methods of amplification are well known in the art.

PCR can be performed as according to Whelan, et al., *J. Clin. Microbiol.*, 33(3):556–561 (1995). Briefly, a PCR reaction mixture includes two specific primers, dNTP, 0.25 Units (U) of Taq polymerase, and 1×PCR Buffer. For every 25 µl PCR reaction, a 2 µl sample (e.g., isolated DNA from target organism) is added and amplified on a thermal cycler. The amplification cycle includes an initial denaturation, and up to 50 cycles of annealing, strand elongation and strand separation (denaturation).

LCR can be performed as according to Moore et al., *J. Clin. Microbiol.*, 36(4):1028–1031 (1998). Briefly, an LCR reaction mixture contains two pair of probes, dNTP, DNA ligase and DNA polymerase representing about 90 µl, to which is added 100 µl of isolated nucleic acid from the target organism. Amplification is performed in a thermal cycler (e.g., LCx® thermal cycler, Abbott Labs, North Chicago, Ill.).

SDA can be performed as according to Walker et al., *Nucleic Acids Res.*, 20(7):1691–1696 (1992). Briefly, an SDA reaction mixture contains four SDA primers, dGTP, dCTP, TTP, dATPS, 150 U of Hinc II, and 5 U of exonuclease deficient *E. coli* DNA polymerase I. The sample mixture is heated 95° C. for 4 minutes (min) to denature target DNA prior to addition of the enzymes. After addition of the two enzymes, amplification is carried out for 120 min at 37° C. in a total volume of 50 µl. The reaction is terminated by heating for 2 minutes at 95° C.

NASBA can be performed as according to Heim et al., *Nucleic Acids Res.*, 26(9):2250–2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 20 µl.

TMA can be performed as according to Wylie et al., *J. Clin. Microbiol.*, 36(12):3488–3491 (1998). In TMA, nucleic acid targets are captured with magnetic beads containing specific capture primers. The beads with captured targets are washed and pelleted before adding amplification reagents, which contain amplification primers, dNTP, NTP, 2500 U of reverse transcriptase and 2500 U of T7 RNA polymerase. A 100 µl TMA reaction mixture is placed in a tube, 200 μl oil reagent is added and amplification is accomplished by incubation at 42° C. in a waterbath for one hour (hr).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, it is important for a single step assay that the nucleic acid releasing reagents and the detection reagents are not potential inhibitors of amplification enzymes if the ultimate detection is to be amplification based.

Also included in the composition for amplification are appropriate nucleoside triphosphates, amplification buffer and certain ions. The concentrations of nucleic acid primers and enzymes can be selected for specific use. For example, for polymerase chain reaction, the concentration of the nucleic acid primer is between 1 picomole and 1 millimole when added to the sample. The enzyme concentration can vary between about 0.01 U and 100,000 U. One skilled in the art can determine the optimal concentration of enzyme and other reagents by routine experimentation.

Detection of the nucleotide sequences also can be performed directly without amplification by hybridizing the sample nucleic acid to the nucleic acid probe present in the composition. In this case, the nucleic acid is contacted and incubated with the labeling reagents (provided in the nucleic acid release composition or separately) and the mixture is irradiated at a particular wavelength for the covalent interaction between the photochemically reactive DNA binding ligand and the test sample to take place. After labeling, the material is hybridized under specified hybridization conditions with a probe specific for the target nucleic acid.

Hybridization of the labeled sample nucleic acid or the labeled nucleic acid probe can be detected in any conventional hybridization assay format and, in general, in any format suitable for detecting the hybridized product or aggregate comprising the labeled nucleic acid. If the sample nucleic acid has been labeled, it can be used for hybridization in solution and solid-phase formats, including, in the latter case, formats involving immobilization of either sample or nucleic acid probe. For example, preimmobilized nucleic acid probe can be hybridized with labeled sample nucleic acid. The presence of label associated with the solid phase indicates hybridization between the probe and the sample nucleic acid and, thus, detection of the target nucleotide sequence. Alternatively, unlabeled sample nucleic acid can be preimmobilized and a labeled probe evaluated for hybridization thereto.

Preferable concentration for the probe is between about 0.01 picomole and 10 millimoles, more preferably between about 1 picomole and 1 millimole, and most preferably between about 10 picomole and 10 micromoles. Methods of detecting hybrids on solid phases are well known in the art and have been extensively described (e.g., U.S. Pat. Nos. 5,232,831, 4,950,613, 486,539 and 4,563,419).

The nucleic acid probe comprises at least one hybridizable, e.g., single-stranded, base sequence substantially complementary to or homologous with the nucleotide sequence to be detected. However, such base sequence need not be a single continuous polynucleotide segment, but can comprise two or more individual segments interrupted by non-homologous sequences. These non-homologous sequences can be linear or they can be self-complementary and form hairpin loops. In addition, the homologous region of the probe can be flanked at the 3'- and 5' termini by non-homologous sequences, such as those comprising the DNA or RNA or a vector into which the homologous sequence had been inserted for propagation. In either instance, the probe as presented as an analytical reagent will exhibit detectable hybridization at one or more points with sample nucleic acids of interest. Linear or circular hybridizable, e.g., single-stranded polynucleotides can be used as the probe element, with major or minor portions being duplexed with a complementary polynucleotide strand or strands, provided that the critical homologous segment or segments are in single-stranded form and available for hybridization with sample DNA or RNA. Useful probes include linear or circular probes wherein the homologous probe sequence essentially is a single-stranded form (Hu et al., *Gene,* 17:271 (1982)).

The nucleic acid probe can be used in any conventional hybridization technique. As improvements are made and conceptually new formats are developed, such can be readily applied to the present probes. Conventional hybridization formats that are particularly useful include those wherein the sample nucleic acids or the polynucleotide probe are immobilized on a solid support (solid-phase hybridization) and those wherein the polynucleotide species are all in solution (solution hybridization).

In solid-phase hybridization formats, one of the polynucleotide species participating in hybridization is fixed in an appropriate manner in its single-stranded form to a solid support. Useful solid supports are well known in the art and include those, for example, which bind nucleic acids either covalently or non-covalently. Non-covalent binding supports, which are generally understood to involve hydrophobic bonding include naturally occurring and synthetic polymeric materials, such as nitrocellulose, derivatized nylon and fluorinated polyhydrocarbons, in a variety of forms such as filters, beads or solid sheets. Covalent binding supports (in the form of filters, beads or solid sheets, just to mention a few) are also useful and comprise materials having chemically reactive groups or groups such as dichlorotriazine, diazobenzyloxymethyl, and the like, which can be activated for binding to polynucleotides.

It is well known that non-covalent immobilization of an oligonucleotide to a solid support such as nitrocellulose paper is generally ineffective for detecting hybridization. Thus, covalent immobilization is preferred and can be achieved by phosphorylation of an oligonucleotide by a polynucleotide kinase or by ligation of the 5'-phosphorylated oligonucleotide to produce multioligonucleotide molecules capable of immobilization. The conditions for kinase and ligation reaction have been described previously (e.g., Sambrook et al., *Molecular Cloning: A Laboratory Manual,* Cold Spring Harbor Laboratory, 1.53 and 5.33, (1989). Thus oligonucleotide probes specific for genetic defects related to hemoglobinopathies, such as sickle cell anemia and alpha-thalassemias can be immobilized on nitrocellulose paper and contacted with patient sample nucleic acid labeled by the above described method. The photochemical labeling can be done in a single step without the need to obtain purified nucleic acid samples and without affecting the specific hybridizability of the labeled sample.

A typical solid-phase hybridization technique begins with immobilization of sample nucleic acids onto the support in single-stranded form. This initial step essentially prevents reannealing of complementary strands from the sample and can be used for concentrating sample material on the support for enhanced delectability. The nucleic acid probe is then contacted with the support and hybridization detected by measurement of the label as described herein. The solid support provides a convenient means for separating labeled probe, which has hybridized to the sequence to be detected, from probe that has not hybridized.

Another method of interest is the sandwich hybridization technique wherein one of two mutually exclusive fragments of the homologous sequence of the probe is immobilized and the other is labeled. The presence of the polynucleotide sequence of interest results in dual hybridization to the immobilized and labeled probe segments (Rankim, et al., 21:77–85 (1983)).

In one embodiment, the immobile phase of the hybridization system can be a series or matrix of spots of known kinds and/or dilutions of denatured DNA. This can be prepared by pipetting appropriate small volumes of native DNA onto a dry nitrocellulose or nylon sheet, floating the sheet on a sodium hydroxide solution to denature the DNA, rinsing the sheet in a neutralizing solution, then baking the sheet to fix the DNA. Before DNA:DNA hybridization, the sheet is usually treated with a solution that inhibits non-specific binding of added DNA during hybridization.

In solid phase detection systems, unhybridized labeled test sample can be removed by washing following hybridization. After washing, the hybrid is detected through the label carried by the test sample, which is specifically hybridized with a specific probe.

In some embodiments, the composition of stabilized cocktail can include reagents to label the released nucleic acid for later detection of formed hybrids essentially as described in U.S. Pat. Nos. 4,950,744 and 5,026,840. Such reagents for labeling nucleic acid comprise a binding ligand comprising a chemical moiety that binds to a nucleic acid and that, when activated by light (i.e. photochemistry), forms at least one covalent bond therewith, a label comprising a detectable moiety and optionally, a binding enhancer comprising a chemical moiety that has a specific affinity for nucleic acids (U.S. patent application Ser. No. 09/265,127, now U.S. Pat. No. 6,187,566 B1, issued Feb. 13, 2001). Covalent or non-covalent complexes of a binding ligand, a binding enhancer and a label is referred to herein as a "LAC."

The nucleic acid binding enhancer ("binding enhancer"), serves to enhance the affinity of the LAC for nucleic acids above that exhibited with the binding ligand alone. Accordingly, binding enhancers tend to have a specific affinity for nucleic acids when compared to non-nucleic acid sample/reaction constituents. The binding enhancer can be the same as or different from the binding ligand. In other words, the binding ligand and the binding enhancer can each be an intercalator, wherein one of the two is a monoadduct-forming species, and the other is present to enhance binding by this monoadduct-forming species. Examples of such "dual role" binding ligands are described in Chaires, et al., J. Med. Chem., 40:261–266 (1977). Therein, it has been described that binding of a bis-intercalating anthracycline antibiotic reached as high as $10^{11}$ at 20° C. It was also shown that the affinity of a similar monointercalator is not above $10^7$ (Chaires, et al., Biochem., 35:2047–2053 (1996)).

The binding enhancer also can be a non-intercalating compound. There are many non-intercalating nucleic acid binding molecules known in the art. A bis-benzimidazole derivative commonly known as Hoechst 33258 has shown affinity as high as $3.2 \times 10^8$ $M^{-1}$ (Haq, et al., J. Mol. Biol., 271:244–257 (1997)). Other non-intercalating binding enhancers are oligo pyrroles, phenyl indole derivatives and the like. These molecules do not bind nucleic acids solely on the basis of positive charge. Other suitable binding enhancers bind nucleic acids on the basis of hydrogen bond formation, hydrophobic interaction in the major or minor groove of the nucleic acid double helix and other non-ionic interactions that give rise to high affinity reactions with nucleic acids.

Not every compound capable of forming an electrostatic bond with a negatively charged nucleic acid can serve as a binding enhancer. For example, polycations such as polyamines are generally not suitable for use in the present invention because of their inability to specifically bind to nucleic acids in crude samples and in the presence of amplification reaction components. Such positively charged compounds can, for example, non-specifically bind to all anionic macromolecules present in the sample, and not just to nucleic acids. In addition, the binding enhancer should be capable of specifically binding to nucleic acids in the presence of 10 to 20 mM magnesium, which is typically required for most amplification reactions. At this concentration, compounds that bind to nucleic acids solely on the basis of electrostatic interactions do not form stable complexes with nucleic acids and thus require a greater concentration of LAC for efficient labeling.

The binding ligand for labeling nucleic acid is either directly or indirectly linked to a label essentially as described in U.S. Pat. Nos. 4,950,744 and 5,026,840. Certain compounds can serve the dual role of a binding enhancer and a linker. For example, linkers can be constructed from positively charged compounds, such that they enhance binding with negatively charged nucleic acids. However, in order for the linker to also serve as a binding enhancer, it is necessary for it to have a specific affinity for nucleic acids, and not just a structure specific electrostatic affinity for negatively charged compounds. The polyalkylamine linkers described in U.S. Pat. No. 5,026,840 are especially useful as binding enhancers, although they can be suitable for use as linkers.

In a preferred embodiment, a bifunctional linker is used that is capable of reacting with both the nucleic acid binding moiety and the label to form a chemical bridge therebetween. However, in an alternate embodiment, a multifunctional linker can be employed, to which the binding ligand, the binding enhancer and the label are attached as a "branched" complex. Such complex formats and chemical reactions for forming these types of complexes are well known in the art.

The present invention also provides methods and kits for using the disclosed compositions in assays for detecting the presence of a nucleotide sequence in nucleic acid of a sample containing cells. Such kits may also include other materials that would make the invention a part of other procedures including adaptation to multi-well technologies. The items comprising the kit may be supplied in separate vials or may be mixed together, where appropriate.

The compositions, methods and kits of the present invention can be used in assays for diagnosis of infectious diseases, cancer, human genetic disorders, and others like histocompatibility (e.g., HLA) typing, forensic and paternity testing. For example, a clinical sample can be contacted with the above described compositions which include a stabilized cocktail of amplification reagents and diagnosis of infectious disease determined. The stabilized cocktail also can include reagents for releasing nucleic acid from cells and appropriate labeling reagents (e.g., LACs) such that the clinical sample can be diagnosed without any further reagent addition. Thus, a urine sample, for instance, that is suspected of bacterial infections can be labeled without centrifugation, filtration or dialysis and the cells in the samples are lysed without any separation step.

Test samples include body fluids, e.g., urine, blood, semen, cerebrospinal fluid, pus, amniotic fluid, tears, or semisolid or fluid discharge, e.g., sputum, saliva, lung aspirate, vaginal or urethral discharge, stool or solid tissue samples, such as a biopsy or chorionic villi specimens. Test samples also include samples collected with swabs from the skin, genitalia, or throat. The compositions of the invention can be added directly to the sample or to cells isolated from the sample.

The assay method can detect the nucleic acid from essentially any species of organism, including, for example, Acintobacter, Actinomyces, Aerococcus, Aeromonas, Alclaigenes, Bacillus, Bacteriodes, Bordetella, Branhamella, Bevibacterium, Campylobacter, Candida, Capnocytophagia, Chlamydia, Chromobacterium, Clostridium, Corynebacterium, Cryptococcus, Deinococcus, Enterococcus, Erysielothrix, Escherichia, Flavobacterium, Gemella, Gonorrhea, Haemophilus, Klebsiella, Lactobacillus, Lactococcus, Legionella, Leuconostoc, Listeria, Micrococcus, Mycobacterium, Neisseria, Nocardia, Oerskovia, Paracoccus, Pediococcus, Peptostreptococcus, Propionibacterium, Proteus, Psuedomonas, Rahnella, Rhodococcus, Rhodospirillium, Staphlococcus, Streptomyces, Streptococcus, Vibrio, and Yersinia. Also included are viruses such as the hepatitis viruses and human immunodeficiency viruses (HIV).

The present methods also can be used to detect nucleic acid from eukaroytes (protists) in samples from higher organisms, such as animals or humans. Eukaroytes include algae, protozoa, fungi and slime molds. The term "algae" refers in general to chlorophyll-containing protists, descriptions of which are found in Smith, *Cryptogamic Botany*, 2nd ed. Vol. 1, Algae and Fungi, McGraw-Hill, (1955). Eukaryotic sequences according to the present invention includes all disease sequences. Accordingly, the detection of genetic diseases, for example, also are embraced by the present invention.

Methods of detecting a nucleotide sequence involve contacting the sample with above described aqueous compositions of a stabilized cocktail and reagents for releasing nucleic acid. The mixture is incubated for an appropriate period of time and under conditions suitable for releasing the nucleic acid from the cells. If the sample already contains released or isolated nucleic acid, only the stabilized cocktail of reagents for amplification need be added.

EXAMPLES

Materials:

The synthesis of several new lipids is described in Examples 1–3, other lipids DOPE (Avanti Polar Lipids); DODMECAP, DOMCATOP, DOMHYTOP, DODMECAP, OBEHYTOP and OBECATOP were prepared as described in PCT WO 96/40627.

The lipids and other materials used in the present invention include the materials described in WO 96/40627 and other commercially available materials. The synthesis of new compounds are described below. Unless indicated otherwise, parts are parts by weight, molecular weight is weight average molecular weight, temperature is in degrees Centigrade, and pressure is at or near atmospheric.

Example 1

Synthesis of 3-(2-aminopropyl-1,3-dihexadecyloxypropyl)hexadecyl ether

This example describes the synthesis of a lipid compound useful for releasing nucleic acids from cells according to the methods and compositions of the invention. A three step procedure is provided as follows.

Step 1. Synthesis of 1,3-dihexadecyloxy-2-aminopropane

A solution of 2-amino-1,3-propanediol (Serinol: Aldrich Chem. Co., Milwaukee, Wis.; Catalog No. 35,789-8) in tetrahydrofuran (THF) is added dropwise with vigorous stirring to a slurry of sodium hydride in THF over a period of 1–2 hrs. The reaction mixture is stirred for an additional 30 minutes to 1 hr at room temperature. Hexadecyl tosylate in THF is added dropwise to the mixture with vigorous stirring over a period of 1–1.5 hrs. The reaction mixture is stirred at room temperature for 1 hr and worked up by addition of isopropanol to destroy excess sodium hydride. The reaction mixture is extracted with chloroform (3×100 mL) and the combined chloroform layers are washed with water (2×50 mL), saturated NaCl (1×50 mL) and dried (MgSO$_4$). The dried chloroform layer is evaporated under vacuum to afford the product as an off-white solid.

Step 2. Synthesis of N-(3-hydroxypropyl)-1,3-dihexadecyloxypropyl-2-amine

The compound from Step 1, above, is dissolved in methylene chloride and added to a solution of 3-bromopropanol in methylene chloride containing triethyl amine with vigorous stirring. The reaction mixture is stirred at room temperature for an additional 8–36 hrs. Upon completion of reaction, as shown by thin layer chromatography (TLC), the reaction mixture is extracted with methylene chloride. The methylene chloride layer is washed with dilute hydrochloric acid (3×50 mL), water (3×100 mL), saturated NaCl (1×75 mL) and dried (MgSO$_4$). The dried methylene chloride is evaporated under vacuum to afford the product as a solid.

Step 3. Synthesis of 3-(2-aminopropyl-1,3-dihexadecyloxypropyl)hexadecyl ether

The compound from step 2, above, is dissolved in THF containing a trace of methylene chloride and is added dropwise with vigorous stirring to a suspension of sodium hydride in THF over a period of 45 minutes to 2 hrs. The reaction mixture is stirred for an additional 1 hr at room temperature. A solution of hexadecyl bromide (Aldrich Chem. Co., catalog No. 23,445-1) in THF is added dropwise with vigorous stirring over a period of 2 hrs. The reaction mixture is stirred for additional 2–4 hrs at room temperature. The reaction mixture is quenched by adding isopropanol and the mixture is worked up by extraction with methylene chloride. The methylene chloride layer is washed in water (3×100 mL), saturated NaCl (1×50 mL) and dried (MgSO$_4$). The dried organic layer is evaporated under vacuum to afford the product as a white solid.

Example 2

Synthesis of 3-(2aminopropyl-1-octadecyloxy-3-benzyloxypropyl)benzyl sulfide

This example describes the synthesis of a lipid compound useful for releasing nucleic acids according to the methods and compositions of the invention. A three step procedure is provided as follows.

Step 1. Synthesis of 1-Octadecyloxy-3-benzyloxy-2-aminopropane

A solution of 2-amino-1,3-propanediol in THF is added dropwise with vigorous stirring to a suspension of sodium hydride over a period of 45 minutes to 2 hrs. The reaction mixture is stirred at room temperature for an additional hr and sequentially treated with a solution of one equivalent each of octadecyl bromide and benzyl bromide, respectively. The reaction mixture is stirred at room temperature for 4–14 hrs. The reaction mixture is worked up by extraction with methylene chloride. The methylene chloride layer is washed with water (3×50 mL), saturated NaCl (1×50 mL) and dried ($MgSO_4$). The dried organic layer is evaporated under vacuum to afford the product as a white solid.

Step 2. Synthesis of 2-N-(3-mercaptopropyl)-amino-1-octadecyloxy-3-benzyloxypropane A solution of 1-octadecyloxy-3-benzyloxy-2-aminopropane from step 1, above, and 3-chloro-1-propanethiol (Aldrich, catalog No. C6,860-1) in methylene chloride containing diisopropylethyl amine is stirred at room temperature for 8–36 hrs. Upon completion of reaction, the reaction mixture is extracted with methylene chloride and washed with dilute acid. The organic layer is washed with water (3×75 mL), saturated NaCl (1×75 mL) and dried ($MgSO_4$). The dried organic layer is evaporated under vacuum to yield a white solid product.

Step 3. Synthesis of 3-(2-aminopropyl-1-octadecyloxy-3-benzyloxypropyl)benzyl sulfide A solution of octadecyl bromide in methylene chloride is added dropwise with vigorous stirring to a solution of the compound from step 2, above, in methylene chloride containing triethyl amine over a period of 45 minutes to 2 hrs. The reaction mixture is stirred for an additional 2–4 hr at room temperature. The reaction mixture is poured into a mixture of ice-water and the mixture is worked up by extraction with methylene chloride. The methylene chloride layer is washed with water (3×100 mL), saturated NaCl (1×50 mL) and dried ($MgSO_4$). The dried organic layer is evaporated under vacuum to yield a white solid product.

Example 3

Synthesis of bis(3-benzyloxypropyl-1-octadecyloxy-3-benzyloxy-2-propyl amine)-polyethyleneglycol The following two steps describe the synthesis of a lipid compound, bis(3-benzyloxypropyl-1-octadecyloxy-3-benzyloxy-2-propyl amine)-pentaoxaheptadecane. This is one member of the class of compounds, bis(3-benzyloxypropyl-1-octadecyloxy-3-benzyloxy-2-propyl amine)-polyethyleneglycol (polyethyleneglycol: "PEG"), which is a conjugate of a membrane fluidizing compound and a lipid. This compound can be used instead of a simple lipid compound in releasing nucleic acid according to the methods and compositions of the invention.

Step 1. Synthesis of pentaoxaheptadecane ditosylate

A solution of p-toluenesufonyl chloride (74 g, 0.39 mol) is added dropwise to a stirred solution containing hexamethylene glycol (50 g, 0.18 mol) trimethylamine (40 g, 0.39 mol) in methylene chloride (400 mL) at 0° C. The reaction mixture is stirred for 1 hr at room temperature. The mixture is filtered and the filtrate is concentrated under vacuum in a rotary evaporator. The residue is suspended in ethylacetate (500 mL) and filtered. The filtrate concentrated under vacuum to afford yellow oil. The yellow oil is triturated with hexane and the resulting oil dried under vacuum to afford 108 g of yellow oil.

Step 2. Synthesis of bis(3-benzyloxypropyl-1-octadecyloxy-3-benzyloxy-2-propylamine)-PEG A solution containing the compound from Example 2, Step 2 and pentaoxaheptadecanoate ditosylate is combined in dimethylformamide containing diisopropylethyl amine and stirred at room temperature for 4–48 hrs. Upon completion of reaction as shown by TLC, the reaction mixture is poured over ice-water. The mixture is stirred for 1–2 hrs and extracted with methylene chloride. The organic layer is washed with dilute acid, water (3×50 mL), saturated NaCl (1×50 mL) and dried ($MgSO_4$). The dried methylene chloride is evaporated under reduced pressure to afford the product as a white solid.

Example 4

Preparation of Aqueous Solutions Formulated with Lipids for Releasing Nucleic Acids This example describes an aqueous solution containing lipids for releasing nucleic acid from cells. 80 micromoles of total lipid (which includes lipid, cholesterol or other sterol, and oleic acid alone or in combination with titratable amphiphile and sterol in 10:5:2 ratio) is dissolved in chloroform and dried. The dried lipid is rehydrated with 1 mL of an aqueous solution of the reagents to be mixed or formulated. Rehydration is performed by vortexing the mixture overnight at 37° Centigrade ("C"). For liposomal preparations, the mixture is further processed by freeze thawing and extruded through polycarbonate filters and further purified by gel filtration. The formulations can be prepared in presence of a reversible amplification inhibitor. Such inhibitors are added when the mixture also contains reagents for an amplification reaction.

Example 5

Preparation of Aqueous Solutions Formulated with Lipids and Enzymes

This example describes a method for preparing aqueous lipid solutions containing enzymes that are useful for releasing nucleic acid according to the methods and compositions of the invention. The following aqueous lipid containing solutions are prepared:

Reagent A:
80 $\mu$l dried lipid (Example 4) and 1 mL of 50 mM Sodium Acetate (pH 6) containing 100,000 units of lysozyme (Sigma Chemical Co., St. Louis, Mo.).

Reagent B:
80 $\mu$l dried lipid (Example 4) and 1 mL of 10 mM Borate (pH 8) containing 100,000 units of lipase (Sigma Chem. Co.).

Reagent C:
80 $\mu$l dried lipid (Example 4) and 1 mL of 10 mM Borate (pH 8) containing 1 mg proteinase K (Sigma Chem. Co.).

Reagent D:
80 $\mu$l dried lipid (Example 4) and 1 mL of 50 mM Sodium Acetate (pH 6) containing 50,000 units each of lysozyme and lipase.

Rehydration is carried out by vortexing the mixture overnight at 37° C. For liposomes, the mixture is further processed by freeze thawing and extrusion through polycarbonate filters (0.1 $\mu$M pore). The formulations can be prepared in presence of a reversible amplification inhibitor. Such inhibitors are used only when the mixture is prepared for an amplification reaction.

Example 6

Preparation of Aqueous Solutions Formulated with Lipids and Enzymes and a Probe

This example describes the preparation of aqueous lipid solutions containing enzymes and a probe that are useful for releasing nucleic acid and hybridizing the nucleic acid to the probe. The following aqueous lipid containing solutions are prepared:

The reagent solution to be mixed or formulated contains an oligonucleotide probe for subsequent hybridization. The reagents include:

Reagent A:
  80 µl dried lipid (Example 4) and 1 mL of 50 mM Sodium Acetate (pH 6) containing 100,000 units of lysozyme (Sigma Chem. Co.) and 1 micromolar of the probe.

Reagent B:
  80 µl dried lipid (Example 4) and 1 mL of 10 mM Borate (pH 8) containing 100,000 units of lipase (Sigma Chem. Co.) and 1 micromolar of the probe.

Reagent C:
  80 µl dried lipid (Example 5) and 1 mL of 10 mM Borate (pH 8) containing 1 mg of proteinase K (Sigma Chem. Co.), 1 mM EDTA and 1 micromolar of the probe.

Reagent D:
  80 µl dried lipid (Example 4) and 1 mL of 50 mM Sodium Acetate (pH 6) containing 50,000 units each of lysozyme and lipase, and 1 micromolar of the probe.

Rehydration is carried out by vortexing the mixture overnight at 37° C. For liposomes, the mixture is further processed by freeze thawing and extruded through polycarbonate filters and further purified by gel filtration. The formulations can be prepared in presence of a reversible amplification inhibitor. Such inhibitors are used only when the mixture is prepared for an amplification reaction.

Example 7

Preparation of Aqueous Solutions for Releasing and Labeling Nucleic Acid

This example describes the preparation of aqueous solutions containing lipids and other compounds for releasing and labeling nucleic acid.

Aqueous solutions containing lipids and formulated with enzymes and other substances as described in Examples 4, 5 and 6 are combined with a photoreative DNA binding ligand, such as BPA (Example 17) or spermine-biotin-angelicin (SBA: Albarella et al., *Nucleic Acids Res.*, 17:4293–4308 (1989)), BPIMA (Example 18), APIMA (Example 19), AZPIMA (Example 20) or BDA (Example 21) at a concentration of about 100 micromolar.

Example 8

Preparation of Aqueous Solutions for Releasing Nucleic Acid and Amplifying Nucleic Acid This example describes the preparation of aqueous solutions containing lipids for releasing and amplifying nucleic acids.

In the lipid containing formulations of Examples 4, 5(A), (B), (C), and 7, additional chemicals for nucleic acid amplification, which include primers, enzymes and nucleoside triphosphates are added. Formulations with enzymes are made with reagents that are free of proteinases and nucleases. The concentrations of each of the amplification components are adjusted on the basis of type of procedure to be followed. For a typical PCR, a five fold higher concentration of materials is used in formulations so that if one fifth of the mixture is used for amplification the final amplification concentration is adjusted to its optimum level.

Example 9

Preparation of an Aqueous Solution for Releasing and Capturing Nucleic Acid on a Solid Phase This example describes the preparation of aqueous solutions containing lipids for releasing and capturing nucleic acids on a solid phase.

Oligo-dT magnetic particles (Novagen, Madison, Wis.) are used as a solid phase for capturing polyA containing RNA from cells. 10 µg of the particles are added to any of Reagents A–D of Examples 5 and 6.

Example 10

Releasing Nucleic Acids from Gram Negative Bacteria Using Aqueous Lipid Solutions

*E. Coli* strain ATCC 35218 (gram negative) is grown in culture medium as described by Isenberg, H. D., (Antimicrobial Susceptibility Testing, ASM press, (1994) pp 5.2.2), to an OD at 600 nm of 1.0. One mL of cell culture is added (in duplicate) to 100 microliters ("µl") of reagent (A) or (B) or (C) or (D) of Example 5. The mixture is incubated at 37° C. for 15 minutes until the absorbency at 600 nm reads less than 0.1 indicating more than 90% lysis.

Example 11

Releasing Nucleic Acids from Gram Positive Bacteria Using Aqueous Lipid Solutions

*Staphylococcus aureus* strain ATCC 29213 (gram positive) is grown as described for *E. Coli* to an OD at 550 nm of 1.0. One niL of cell culture is added (in duplicate) to 100 microliters ("µl") of reagent (A) or (B) or (C) or (D) of Example 5. The mixture is incubated at 60° C. for 15 minutes until the absorbency at 550 nm reads less than 0.1 indicating more than 90% lysis.

Example 12

Releasing Nucleic Acids from a Clinical Sample Containing *Chlamydia Trachomitis*

Cervical swabs samples are collected in transport medium (Manual of Clinical microbiology, 5$^{TH}$ Ed., ASM press (1991), p1238) lacking any detergent. 0.2 mL of Reagent A described in Example 5 is added to the medium containing the swab. The mixture is incubated at 37° C. for 15 min. 100 µl of the mixture is then subjected to Gen-Probe's commercial PACE 2 assay format (Gen-Probe, Inc., San Diego, Calif.) according to the manufacturer's instructions. The results support efficient release of RNA as judged by the hybridization assay.

Example 13

Releasing, Labeling and Detecting Nucleic Acid from a Clinical Sample Suspected of Chlamydial Infection Cervical swabs samples are collected in transport medium lacking any detergent as described in Example 12. 0.2 mL of the aqueous solution containing BPA described in Example 7 is added to the medium containing the swab. The mixture is incubated at 37° C. for 60 minutes. During the incubation step, the sample is exposed to light of 340±30 nm using a transilluminator. After illumination, the labeled sample is hybridized with the PACE 2 probe (Gen-Probe, Inc., San Diego, Calif.), immobilized to nitrocellulose paper. The presence of the label on the nitrocellulose indicates hybridized nucleic acids and demonstrates the effectiveness of the simultaneous lysis and labeling of the released nucleic acids.

Example 14

Releasing Nucleic Acids from a Clinical Sample Infected with *Mycobacterium Tuberculosis*

A sputum sample from a tuberculosis positive individual is processed by treatment with N-Acetyl-L-cysteine-NaOH to generate a sediment as described in the Manual of Clinical microbiology, 5$^{th}$ Ed., ASM press (1991), p307–309. 100 µl of the sediment is added to 10 µl of reagent (D) in Example 5 and 90 µl of Tris buffer pH 7.4±0.2. A control extraction sample is prepared containing 100 µl of the sediment and 100 µl of the Tris buffer. The mixtures are incubated at 60° C. for 1 hr and then heated at 90° C. for 15 minutes. The control sample is lysed by sonication. The samples are then tested by PCR as described in Christian et al., *J. Clin. Microbiol.* 33(3):556–561 (1995). The results indicate efficient lysis of both samples.

Example 15

Releasing, Labeling and Detecting Nucleic Acid from a Urine Sample with an Aqueous Lipid Solution This example demonstrates releasing, labeling and detecting nucleic acids from a urine sample with Reagent A of Example 7 (Reagent A contains and BPA as the labeling agent). Urine is processed by centrifugation as described in Dattagupta, et al., *Analytical Biochemistry*, 177:85–89 (1989), and resuspended in 50 mM sodium acetate buffer pH 6. 0.9 mL of the suspension is added to 0.1 mL of Reagent A and the mixture is incubated at 37° C. for 2 hrs. The step of photoactivation and detection of the labeled product is performed as described by Dattagupta, et al. supra (1989). Briefly, after nucleic acid is released (or during incubation), the mixture is exposed to light (365±30 nm) for 60 minutes to conjugate the BPA to the nucleic acid. The labeled nucleic acid is then hybridized to a specific probe.

Example 16

Releasing and Labeling Nucleic Acid from a Clinical Serum Sample Suspected of Containing Hepatitis B Virus This example demonstrates releasing and labeling nucleic acid from a serum sample with an aqueous solution comprising BPA prepared as described in Example 7 (based on any of Regents A–D from Examples 5 or 6) is added to 50% v/v. 100 µl of the serum sample is added to 100 µl of the aqueous solution and the mixture heated at 60° C. for 10 minutes. The step of photoactivation and detection of the labeled product is performed as described by Dattagupta, et al.,*Analytical Biochemistry,* 177:85–89 (1989). Briefly, after nucleic acid is released (or simultaneously with incubation), the mixture is exposed to light (365±30 nm) for 60 minutes to conjugate the BPA to the nucleic acid. The labeled nucleic acid is then hybridized to immobilized genomic hepatitis B DNA and detected as described in Dattagupta et al., supra (1989).

Example 17

Preparation of 4'-Biotinyl-pentaoxaheptadecane -4, 5'-dimethylangelicin (BPA)

This example describes the preparation of the photoreactive nucleic acid binding ligand, BPA.

The synthesis of BPA is carried out in the following five steps.

Step 1: Preparation of 3,6,9,12,15-pentaoxaheptadecane-1,17-diol ditosylate

A solution of 73.91 g of p-toluenesulfonyl chloride (0.389 mol) in 400 mL of methylene chloride is added dropwise with stirring over a 2.5 hrs period to 400 mL of methylene chloride containing 50 g of hexaethylene glycol (0.177 mol) and 64 mL of triethylamine (39.36 g, 0.389 mol) at 0° C. The mixture is stirred for one hr at 0° C. and heated to ambient temperature for 44 hrs. The mixture is filtered and the filtrate concentrated in vacuo. The resulting residue is suspended in 500 mL of ethyl acetate and filtered. The filtrate is concentrated in vacuo to a yellow oil which was triturated eight times with 250 mL portions of warm hexane to remove unreacted p-toluenesulfonyl chloride. The resulting oil is then concentrated under high vacuum to yield 108.12 g of a yellow oil (quantitative yield).

Analysis:

Calculated for $C_{26} H_{38} O_{11} S_2$: Calc.=C, 52.87; H, 6.48. found: C, 52.56; H, 6.39.

PMR ("proton magnetic resonance"): (60 MHz, $CDCl_3$) δ: 2.45 (s, 6H); 3.43.–3.8 (m, 20H); 4.2 (m, 4H); 7.8 (AB quartet, J=8 Hz, 8H).

IR ("infrared"): (neat) $cm^{-1}$: 2870, 1610, 1360, 1185, 1105, 1020 930, 830, 785, 670.

Step 2: Preparation of 1,17-Diphthalimido 3,6,9,12, 15-pentaoxaheptadecane

A stirred suspension containing 108 g of 3,6,9,12,15-pentaoxaheptadecane-1,17-diol ditosylate (0.183 mol), 74–57 g of potassium phthalimide (0.403 mol), and 700 mL of dimethylacetamide is heated at 160–170° C. for 2 hrs and then cooled to room temperature. The precipitate is filtered and washed with water and acetone to yield 53.05 g of product as a white powder which was dried at 55° C. (0.1 mm); melting point: 124–126° C.

A second crop of product is obtained from the dimethylacetamide filtrate by evaporation in vacuo and the resulting precipitate is successively washed ethyl acetate, water, and acetone. A resulting white powder is dried at 55° C. (0.1 mm of vacuum) to yield an additional 9.7 g of product; melting point 124.5–126.5° C. The combined yield of product is 62.82 g (68% yield).

Analysis:

First crop, calculated for $C_{28} H_{32} N_2 O_9$ .1/2$H_2O$; Calc.= C, 61.19; H, 6.05; N, 5.09. found: C, 61.08; H 6.15; N, 5.05.

Second crop calculated for $C_{28} H_{32} N_2 O_9$: Calc.=C, 62.21; H, 5.97; N, 5.18. found: C, 61.78; H, 6.15; N, 5.13.

Second Crop PMR: (60 MHz, DMSO-$d_6$) δ: 3.5 (s, 8H); 3.6 (s, 8H); 3.8 (bt, J=3 Hz, 8H): 8.1 (s, 8H).

Second Crop IR: (KBr) $cm^{-1}$: 2890, 1785, 1730, 1400, 1100, 735.

Step 3: Preparation of 1,17-Diamino-3,6,9,12,15-Pentaoxaheptadecane

The synthesis generally followed the method of Kern et al., *Makrol. Chem.,* 180, 2539 (1979). A solution containing 60 g of 1,17-diphthalimido-3,6,9,12,15-pentaoxaheptadecane (0.118 mol), 14.8 g of hydrazine hydrate (0.296 mol), and 500 mL of ethanol is heated with mechanical stirring in a 100° C. oil bath for three hrs. The mixture is cooled and filtered. A resultant filter cake is washed four times with 300 mL portions of ethanol. The combined filtrates are concentrated to yield 32.35 g of a yellow opaque glassy oil by evaporative distillation at 150–200° C. (0.01 mm of vacuum). The result is 22.82 g of a light yellow oil (69% yield). b.p. 175–177° C. (0.07 mm).

Analysis:

For $C_{12} H_{12} N_2 O_5 \cdot 1/2H_2O$: Calc.=C, 49.80, H, 10.10; N, 9.68. found: C, 50.36; H, 9.58; N, 9.38.

PMR: (60 MHz, $CDCl_3$) δ: 1.77 (s, 4H, $NH_2$); 2.85 (t, J=5 Hz, 4H); 3.53 (t, J=5 Hz, 4H); 3.67 (m, 16H).

($CHCl_3$) $cm^{-1}$: 3640, 3360, 2860, 1640, 1585, 1460, 1350, 1250, 1100, 945, 920, 870.

Step 4: Preparation of 1-Amino-17-N-(Biotinylamido)-3,6,9,12,15-pentaoxaheptadecane A solution containing 7.2 g of 1,17-diamino-3,6,9,12,15-pentaoxaheptadecane (25 mmol) in 75 mL of dimethylformamide ("DMF") under an argon atmosphere is treated with 3.41 g of N-succinimidyl biotin (10 mmol) added in portions over 1.0 hour. The resulting solution is stirred for four hrs at ambient temperature. A sample of the solution run on TLC ($SiO_2$; solvent: 70:10.1 $CHCl_3$—$CH_3OH$-conc. $NH_4OH$) and visualized by dimethylaminocinnamaldehyde spray reagent to determine conversion to a new product (Rf=0.18). The solution is divided in half and each half absorbed onto $SiO_2$ and purified by flash column chromatography on 500 g of $SiO_2$-60 (230–400 mesh) using a 70:10.1 $CHCl_3$—$CH_3OH$-conc. $NH_4OH$ solvent mixture. Fractions containing the product are pooled and concentrated to a yield 2.42 g of a gelatinous, waxy solid. The product is precipitated as a solid from isopropanol-ether, washed with hexane, and dried at 55° C. (0.1 mm) to result in 1.761 g of a white powder (35% yield).

Analysis:

Calculated for $C_{22} H_{42} N_2 O_7 S \cdot 3/2H_2O$: Calc.=C, 49.51; H, 8.50; N. 10.49. found: C, 49.59; H, 8.13; N, 10.39.

PMR: (90 MHz, DMSO-$d_6$) δ: 1.1–1.7 (m, 6H); 2.05 (t, J=7 Hz, 2H); 2.62 (t, J=4 Hz, 1H); 2.74 (t, J=4 Hz, 1H); 3.0–3.4 (m, 14H). 3.50 (s, 14H); 4.14 (m, 1H); 4.30 (m, 1H); 6.35 (d, J=4 Hz, 1H); 7.80 (m, 1H).

CMR: (22.5 MHz, DMSO-$d_6$) δ: 25.2, 28.0, 28.2, 35.1, 40.6, 55.3, 59.2, 61.1, 69.6, 69.8, 71,2, 162.7, 172.1.

IR: (KBr) $cm^{-1}$: 2900, 2850, 1690, 1640, 1580, 1540, 1450, 1100.

Mass Spectrum (FAB) m/e: 507.3 (M+1, 56%)

Step 5: Preparation of 4'-Biotinyl-pentaoxaheptadecane-4,5'-dimethylangelicin (BPA)

The synthesis generally followed the method of Albarella, J. P., et al., *Nucl. Acids Res.*, 17:4293 (1989). A solution of 203 mg of 1-amino-17-N-(biotinylamido)-3,6,9,12,15-pentaoxaheptadecane (0.4 mmol) in 1 mL of DMF under an argon atmosphere is treated with 78 mg of N,N-carbonyldimidazole (0.48 mmol). The resulting mixture is stirred for four hrs and then treated with 55 mg of 4'-aminomethyl-4,5'dimethylingelicin hydrochloride (0.2 mmol), 140 μl of diisopropylethylamine, and 100 μl of DMF. The resulting mixture is stirred overnight at 50° C. and then evaporated onto $SiO_2$ in vacuo and the resultant solid is purified by chromatography on 60 g of $SiO_2$ (230–400 mesh), and eluted with 1.5 liters of 7% $CHCl_3$—$CH_3OH$, followed by 1 liter of 10% $CHCl_3$—$CH_3OH$. Fractions containing the product are pooled and concentrated to yield 72 mg of a glassy solid (47% yield).

Analysis:

PMR: (90 MHz, DMSO-$d_6$) : δ.1.1–1.8 (m, 6H); 2.04 (bt, J=7 Hz, 2H); 2.5 (s, 6H); 2.56 (m, 1H); 2.74 (bd, J=4 Hz, 1H); 2.8–3.4 (m, 14H); 3.40 (m, 14H); 4.14 (m, 1H); 4.25 (m, 1H); 4.40 (bd, J=6Hz, 2H); 6.5 (m, 1H); 6.35 (s, 1H); 7.02 (s, 1H); 7.45 (d, J=8 Hz, 1H); 7.62 (d, J=8Hz, 1H); 7.80 (m, 1H).

CMR: (22.5 MHz, DMSO-$d_6$) δ: 11.9, 18.9, 25.3, 28.2 28.3, 33.4, 35.2, 55.4, 59.2, 61.0, 69.2, 69.6, 69.8, 70.0, 89.0, 107.8, 112.0, 113.1, 114.3, 120.6, 121.6, 153.6, 154.4, 155.6. 157.9, 159.5, 162.7, 172.1.

Example 18

Synthesis of angelicin bisbenzimidazole-pentaoxaheptadecane-biotin ("BPIMA")

This example describes the preparation of BPIMA, a LAC comprising a photoreactive binding ligand, binding enhancer and a label. The label is biotin and the enhancer moiety is bisbenzimidazole.

The synthesis of BPIMA is carried out in the following eight steps.

Step 1: Synthesis of dihexadecyl-3-bromo-propanediol

In a 210 mL round bottomed flask equipped with a magnetic stir bar, 2 g of dihexadecylglycerol (Sigma Chem. Co.) is dissolved into 120 mL of toluene. To this solution is added 3.54 g (10.7 mmoles) of carbon tetrabromide and 2.80 g (10.7 mmoles) of tripenylphosphine and the reaction mixture is stirred overnight for 18–20 hrs at room temperature. A resulting yellow suspension is filtered and the filtrate concentrated on a rotary evaporator to afford a white solid residue. This residue is dissolved in toluene, washed once with saturated sodium chloride, dried over anhydrous magnesium sulfate and concentrated under vacuum on a rotary evaporator to afford 2.5 g of crude product as a white powder. This crude product is purified further by flask column chromatography on a silica gel 60 (E. Merck, Germany) column by sequential elution with 100 mL each of hexane, 14 ethyl acetate in hexane, 21 ethyl acetate in hexane and, finally, 31 ethyl acetate in hexane. Fractions (8 mL) are collected and screened by TLC (silica gel; solvent: 5:1 ethyl acetate-hexane) and those fractions that contain pure product are pooled. The pooled fractions are concentrated under vacuum on a rotary evaporator to afford a quantitative yield of 1,2-0-dihexadecyl-3-bromo-1,2 propanediol as a white powder.

Step 2: Synthesis of Bisbenzimidazole Succinate Ester

A solution of bisbenzimidazole (6 g; 0.01 mol) dicyclohexylcarbodiimide (0.05 mol) and Succinic acid (0.01 mol) in 100 mL chloroform is stirred overnight for 18–24 hrs. During this time, a white precipitate is formed. The precipitate is filtered and washed with chloroform (2×50 mL). The chloroform washes are combined and concentrated under vacuum in a rotary evaporator and the residue purified by flash column chromatography. The fractions containing the product are combined and concentrated under vacuum in a rotary evaporate to afford bisbenzimide succinnate ester (80%) as a white solid.

Step 3: Synthesis of pentaoxaheptadecane ditosylate

A solution of p-toluenesufonyl chloride (74 g; 0.39 mol) is added dropwise to a stirred solution containing hexamethylene glycol (50 g; 0.18 mol) trimethylamine (40 g; 0.39 mol) in methylene chloride (400 mL) at 0° C. The reaction mixture is then stirred for 1 hr at room temperature. The mixture is filtered and the filtrate concentrated under vacuum in a rotary evaporator. The residue is suspended in ethylacetate (500 mL) and filtered. The filtrate is concentrated under vacuum to afford yellow oil. The yellow oil is triturated with hexane and the resulting oil vacuum dried to afford 108 g of yellow oil.

Step 4: Synthesis of Diphthalimido pentaoxaheptadecane ditosylate

A suspension of ditosylate (Step 3; 108 g), potassium phthalimide (75 g) in dimethylacetamide (700 mL) is heated at 165° C. for 2 hrs with vigorous stirring. The reaction mixture is then cooled to room temperature and the precipitate filtered. The precipitate is washed with water and acetone to afford 53 g of the desired product as a white solid.

Step 5: Synthesis of Diaminopentaoxaheptadecane (PEG)

A solution of diphthalimide (Step 4: 60 g), hydrazine hydrate (15 g) and ethanol (500 mL) is heated at 100° C. with stirring for 3 hrs. The reaction mixture is cooled to room temperature and filtered. The solid is washed with cold ethanol. The combined filtrate is concentrated under vacuum in a rotary evaporator to afford 33 g of yellow oil.

Step 6: Synthesis of 1-Amino-17-N-(Biotinylamido)-pentaoxaheptadecane

A solution of diaminopentaoxaheptadecane (Step 5: 7 g) in dimethyformamide is mixed with 3.4 g of N-succinimidylbiotin and then stirred at room temperature for 4 hrs. The product is purified by flash column chromatography on a silica gel 60 column. The fractions containing the product are pooled and concentrated under vacuum in a rotary evaporator to afford 2.5 g of a waxy solid. The waxy solid is recrystallized from isopropanol/ether mixture to afford 1.8 g of white powder.

Step 7: Synthesis of bisbenzimidazole-PEG-biotin

A solution of biotinylamido pentaoxaheptadecane (Step 6; 3 g), bisbenzimidazole succinate ester (Step 2; 2 g) and dicydclohexylcarbodiimide (5 g) in chloroform (200 mL) is stirred at room temperature for 20–24 hrs. The white precipitate formed is filtered and the precipitate washed with chloroform. The chloroform washes are combined and concentrated under vacuum in a rotary evaporator and the residue purified by flash column chromatography. The fractions containing the product are combined and concentrated under vacuum in a rotary evaporator to afford bisbenzamide-PEG-biotin as an off-white solid (1.5 g).

Step 8: Synthesis of Angelicin bisbenzimidazole-PEG-biotin

To a solution of bisbenzimidazole-PEG-biotin (Step 7; 0.4 mmol) in dimethylformamide is added N,N-carbonyldiimidazole (0.5 mmol). The resulting mixture is stirred for 3–5 hrs and is then treated with aminomethylangelicin (0.2 mmol), diisopropylethylamine (150 mL) and dimethylformamide (100 mL). The reaction mixture is stirred overnight at 50–55° C. The mixture is evaporated under vacuum in a rotary evaporator and the residue is loaded onto a column of silica gel and eluted sequentially with 7% methanol in chloroform and 10% methanol in chloroform. The fractions containing the product are pooled and concentrated to afford (0.2 mmol) BPIMA as a glassy solid.

Example 19

Synthesis of Angelicin bisbenzimidazole-pentaoxaheptadecane-acridine ("APIMA")

This example describes the preparation of APIMA, a LAC comprising a photoreactive binding ligand, binding enhancer and label. The label is a chemiluminescent acridinium ester.

The following six steps describes the synthesis of APIMA.

Step 1: Synthesis of acrdinecarbonylchloride

A solution of acridine carboxyl acid (Aldrich Chem. Co.) and thionyl chloride is stirred at room temperature for 20–24 hrs. Excess thionyl chloride is removed under vacuum in a rotary evaporator. The residue is treated with toluene and evaporated to remove traces of thionyl chloride.

Step 2: Synthesis of acridine-4-hydroxypropionic acid succinimide ester

A solution of acridine carbonyl chloride(Step 1: 2.3 g) in dry pyridine (35 mL) is treated with hydroxyphenolpropionic acid N-hydroxysuccinimide ester (2.5 g) at room temperature for 8–24 hrs. The resulting triethylaminehydochloride is filtered and the solution is concentrated under vacuum in a rotary evaporator to afford the succinimide ester as an off white solid.

Step 3: Synthesis of methyl fluorosulfonate succinimido acridine

A solution of succinimide ester (Step 2; 2 g) and methyl fluorosulfonate (3 mL) in dry chloroform is stirred for 8–24 hrs at room temperature. The resulting solid is filtered and the solution concentrated under vacuum in a rotary evaporator to afford 1.5 g of product as a yellow solid.

Step 4: Synthesis of 1-Amino-17-N(acridnylamido)-pentaoxaheptadecane

A solution of diaminopentaoxaheptadecane (a "PEG": step 5, Example 18) in dimethylformamide (75 mL) is treated with acridine NHS ester (step 3).

The resulting solution is stirred at room temperature for 4 hrs. The solvent is removed under vacuum in a rotary evaporator and the residue is triturated with hexane to afford the compound as a pale yellow solid.

Step 5: Synthesis of bisbenzimidazole-PEG-acridine

A solution of acridinylamido pentaoxaheptadecane (step 4), bisbenzimidazole succinic acid half ester (step 2, Example 18) and dicyclohexylcarbodiimide in chloroform is stirred at room temperature for 18–24 hrs. A white precipitate is filtered and the precipitate washed with chloroform. The combined chloroform washes are concentrated under vacuum in a rotary evaporation to afford the product as an off white solid.

Step 6: Synthesis of angelicin bisbenzimidazole-PEG-acridine

N,N-carbonyldiimidazole is added to a solution of bisbenzimidazole-PEG-acridine (step 5) in dimethylformamide. The resulting mixture is stirred for 3–8 hrs and then treated with aminomethyldimethylangelicin, diisopropylethylamine and dimethylformamide. The mixture is stirred overnight at 50–55° C. and evaporated under vacuum in a rotary evaporator. The residue is purified by flash column chromatography on a column of silica gel. Sequential elution with 7% methanol in chloroform and 10% methanol in chloroform affords fractions containing the product. The fractions are pooled and concentrated to yield APIMA as a solid.

Example 20

Synthesis of angelicin-bisbenzimidazole-pentaoxaheptadecane-azidonitrobenzene ("AZPIMA")

This example describes the preparation of a AZPIMA, a LAC comprising a photoreactive binding ligand and a binding enhancer, both of which are intercalating moieties.

The following two steps describes the synthesis of AZPIMA.

Step 1: Synthesis of bisbenzimidazole-PEG-azidonitrobenzene

A solution of diaminopentaoxaheptadecane (a "PEG": Step 5, Example 18) and sulfoSANPH® (Pierce Chemicals, Rockford, Ill.) is stirred at room temperature overnight. The solution is concentrated under vacuum in a rotary evaporator and the residue is dissolved in DMF. The solution is treated with bisbenzamide succinate ester (step 2, Example 18) and stirred overnight. Following completion of reaction as determined by TLC, the solution is concentrated to afford an off white crystalline solid.

Step 2: Synthesis of angelicin bisbenzimidazole-PEG-azidonitrobenzene

A solution of bisbenzimidazole-PEG-azidonitrobenzene (Step 1, above) and N,N-carbonyldiimidazole in dimethylformamide is stirred for 4–14 hrs at room temperature. The resulting mixture is treated with aminomethyldimethylangelicin, diisopropylethylamine and the resulting mixture is stirred overnight at 50–55° C. Following completion of reaction, the reaction mixture is concentrated in a rotary evaporator. The residue is purified by flash column chromatography on a column of silica gel. The column is eluted with a mixture of chloroform/methanol and the fractions containing APIMA are pooled and concentrated to afford APIMA as a solid.

Example 21

Synthesis of Angelicin-4',6'-diamidino-2-phenylindole-Biotin ("BDA")

This example describes the preparation of BDA, as LAC comprising a photoreactive binding ligand, binding enhancer and a label.

The following two steps describes the synthesis of BDA.

Step 1: Synthesis of 1-4',6'-diamidino-2-phenylindole 17-pentaoxaheptadecane tosylate (4', 6'-diamidino-2-phenylindole: "DAPI").

A solution of pentaoxaheptadecane ditosylate (Step 3, Example 18) and DAPI (Aldrich Chem. Co., Cat.No 21,708-5) in dimethylsulfoxide is stirred at room temperature for 8–24 hrs. Upon completion of the reaction, as shown by TLC, the mixture is evaporated under vacuum in a rotary evaporator and the residue loaded onto a column of silica gel and eluted with a solution of 0–50% methanol in chloroform. The fractions containing the product are pooled and concentrated under vacuum in a rotary evaporator to afford the product as an off-white solid.

Step 2: Synthesis of Angelicin-DAPI

A solution of 1-DAPI-17-pentaoxaheptadecane tosylate (step 1) and aminomethyldimethylangelicin in dimthylformamide is stirred at 25–60° C. for 8–48 hrs. Upon completion of the reaction, as shown by TLC, the reaction mixture is evaporated under vacuum in a rotary evaporator and the residue is loaded onto a column of silica gel and eluted with a solution of 0–30% methanol in chloroform containing a trace of ammonia. The fractions containing the product are pooled and concentrated to afford the product as a pale yellow solid. The crude product is recrystallized from a mixture of dimethylformamide and hexane.

Step 3: Synthesis of Angelicin-DAPI-Biotin

A solution of angelicin-DAPI (Step 2) and biotin-NHS ester (Sigma Chem. Co., Cat.No. 1759) in DMF is stirred at 25–70° C. for 8–72 hrs. Upon completion of the reaction, the reaction mixture is evaporated under vacuum in a rotary evaporator and the residue is treated with petroleum ether. The solid is collected by filtration and washed with petroleum ether (3×50 mL). The crude solid is recrystallized to afford BDA as a white solid.

Example 22

Reversible Inhibition of Nucleic Acid Amplification by 4'-aminomethyltrioxsalen ("AMT")

This example describes reversible inhibition of a PCR using a DNA binding ligand, 4'-aminomethyltrioxsalen ("AMT").

AMT is purchased from Sigma Chem. Co., St. Louis, Mo. A stock solution of 5 mg/mL AMT is prepared in de-ionized water. An amplification cocktail is prepared containing 200 picomoles of primers Tb11 and Tb12 (Devallois et al., *J. Clin. Microbiol.*, 35:2669–73 (1997)), 1.25 units of Taq polymerase/100 µL, 200 µM dNTPs and 0.05 mg/mL AMT in a Tris-EDTA buffer, pH 7. A corresponding solution without AMT is prepared as a control.

Amplification is performed in Eppendorf tubes to which are added 0.5 µg of whole genomic mycobacterial DNA in 50 µl of buffer and either 1 µl or 10 µl of the amplification cocktail. Final volume is adjusted to 100 µl with the aqueous buffer solution (without AMT) so that the final concentrations of all PCR components, except AMT, is the same in all replicates. Controls received an amplification cocktail without AMT.

PCR amplification is performed for 45 cycles (92° C.–56° C.–72° C.; denaturation, annealing, extension) and the product analyzed by gel electrophoresis. The final concentrations of AMT in the PCR reaction is 5 µg/mL (10 µl addition of stock) and 0.5 µg/mL (1 µl addition of stock).

The results show complete inhibition of the PCR in reactions containing 5 µg/mL AMT. In contrast, detectable amplification product is produced in PCR containing 0.5 µg/mL AMT. The amount of amplification product continues to increase when PCR is performed at lower concentrations of AMT (i.e., 5 ng/mL and 0.5 ng/mL AMT).

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

We claim:

1. A composition for performing nucleic acid amplification that avoids undesirable reactions between the individual reagents, comprising one or more reagents necessary to perform nucleic acid amplification and an inhibitory concentration of a reversible inhibitor(s) of the undesirable reaction, wherein the reagents necessary to perform nucleic acid amplification are encapsulated in liposome vesicles.

2. The composition of claim 1, which comprises one or more nucleic acid polymerase(s) or ligase(s), one or more nucleoside triphosphate(s), one or more nucleic acid primer (s) and an amplification buffer.

3. The composition of claim 1, which comprises all the reagents necessary to perform a nucleic acid amplification reaction.

4. The composition of claim 1, wherein said inhibitor is a nucleic acid binding ligand.

5. The composition of claim 4, wherein said nucleic acid binding ligand is an intercalator compound.

6. The composition of claim 5, wherein the intercalator compound is monoadduct forming.

7. The composition of claim 5, wherein said intercalator compound is a furocoumarin or a phenanthridine.

8. The composition of claim 7, wherein said furocoumarin is 4'-aminomethyltrioxsalen (AMT).

9. The composition of claim 7, wherein said furocoumarin is an angelicin derivative.

10. The composition of claim 4, wherein said binding ligand is a non-intercalating compound.

11. The composition of claim 10, wherein said non-intercalating compound is selected from the group consisting of benzimides, netropsins and distamycins.

12. A method of amplifying a nucleic acid, comprising:
adding a nucleic acid template to be amplified to the composition of claim 1, and optionally a diluent in sufficient amounts to lower the inhibitor concentration to such that it does not substantially inhibit the amplification reaction; and incubating the mixture under conditions sufficient to achieve amplification.

13. A method for preparing a composition for performing nucleic acid amplification that avoids undesirable reactions between the individual reagents, comprising mixing one or more reagents necessary to perform nucleic acid amplification with a reversible inhibitor(s) of the undesirable reaction, wherein the inhibitor is added to the composition at a concentration that is inhibitory to the undesirable reaction but at a concentration which will be non-inhibitory when the composition is later diluted, and wherein the reagents necessary to perform nucleic acid amplification are encapsulated in liposome vesicles.

14. The method of claim 13, wherein said nucleic acid amplification is selected from the group consisting of: polymerase chain reaction, ligase chain reaction, transcription based amplification reaction, nucleic acid sequence based amplification reaction and strand displacement amplification reaction.

15. The method of claim 13, wherein said nucleic acid amplification is a transcription based amplification reaction and said inhibitor(s) is phosphate ion.

16. The method of claim 13, wherein said nucleic acid amplification is a ligase chain reaction and said inhibitor(s) is phosphate ion at a concentration of 1.25 mM.

17. The method of claim 13, wherein said inhibitor is a nucleic acid binding ligand.

18. The method of claim 13, wherein said nucleic acid binding ligand is an intercalator compound.

19. The method of claim 13, wherein said intercalator compound is 4'-aminomethyltrioxsalen (AMT).

20. The method of claim 13, wherein said nucleic acid binding ligand is a non-intercalator compound.

21. A kit comprising a vial containing the composition of claim 1.

22. The kit of claim 21, wherein the composition comprises one or more nucleic acid polymerase or ligase, one or more nucleoside triphosphate(s), one or more nucleic acid primer(s) and an amplification buffer.

23. The kit of claim 21, wherein said inhibitor is a nucleic acid binding ligand.

* * * * *